(12) United States Patent
Coates

(10) Patent No.: US 7,744,906 B2
(45) Date of Patent: Jun. 29, 2010

(54) PAIN RELIEF AGENTS

(75) Inventor: Anthony Robert Milnes Coates, London (GB)

(73) Assignee: Helperby Therapeutics Limited, London (GB)

( * ) Notice: Subject to any disclaimer, the term of this patent is extended or adjusted under 35 U.S.C. 154(b) by 574 days.

(21) Appl. No.: 10/534,054

(22) PCT Filed: Nov. 5, 2003

(86) PCT No.: PCT/GB03/04774

§ 371 (c)(1),
(2), (4) Date: Mar. 22, 2006

(87) PCT Pub. No.: WO2004/041304

PCT Pub. Date: May 21, 2004

(65) Prior Publication Data

US 2006/0252681 A1 Nov. 9, 2006

(30) Foreign Application Priority Data

Nov. 8, 2002 (GB) ................................ 0226105.5

(51) Int. Cl.
*A61K 39/04* (2006.01)
*C07K 14/00* (2006.01)
*C07K 17/00* (2006.01)
*C07H 21/04* (2006.01)
*C07H 21/02* (2006.01)

(52) U.S. Cl. ...................... 424/248.1; 424/9.1; 424/9.2; 424/184.1; 424/185.1; 424/243.1; 530/300; 530/350; 536/23.1; 536/23.7

(58) Field of Classification Search .................. 424/9.1, 424/9.2, 184.5, 185.1, 243.1, 248.1; 530/300, 530/350; 536/23.1, 23.7
See application file for complete search history.

(56) References Cited

U.S. PATENT DOCUMENTS

| | | | |
|---|---|---|---|
| 4,440,859 A | 4/1984 | Rutter et al. | |
| 4,530,901 A | 7/1985 | Weissmann | |
| 4,582,800 A | 4/1986 | Crowl | |
| 4,677,063 A | 6/1987 | Mark et al. | |
| 4,678,751 A | 7/1987 | Goeddel | |
| 4,704,362 A | 11/1987 | Itakura et al. | |
| 4,710,463 A | 12/1987 | Murray | |
| 4,757,006 A | 7/1988 | Toole, Jr. et al. | |
| 4,766,075 A | 8/1988 | Goeddel et al. | |
| 4,810,648 A | 3/1989 | Stalker | |
| 5,856,305 A | 1/1999 | Lucietto et al. | |
| 6,117,421 A | 9/2000 | Morton et al. | |

FOREIGN PATENT DOCUMENTS

| WO | WO 96/16083 A1 | 5/1996 |
|---|---|---|
| WO | WO 99/35270 A1 | 7/1999 |
| WO | WO 01/04344 A2 | 1/2001 |
| WO | WO 02/40037 A | 5/2002 |
| WO | WO 02/40037 A2 | 5/2002 |
| WO | WO 02/40038 A2 | 5/2002 |
| WO | WO 02/40517 A2 | 5/2002 |
| WO | 2009/106819 A2 | 9/2009 |

OTHER PUBLICATIONS

B. Henderson et al, "Molecular Chaperones and Disease", Inflammation Research, vol. 45, No. 4, (1996), pp. 155-158.
F. J. Andrews, et al., "Effect of iron chelation on inflammatory joint disease", Annals of the Rheumatic Diseases, 46, 327-333, (1987).
P. N. Baird, et al., "Cloning and Sequence Analysis of the 10 kDa Antigen Gene of *Mycobacterium tuberculosis*", Journal of General Microbiology 135, 931-939, (1989), XP-008005161.
P. N. Baird, et al., "A major antigen from *Mycobacterium tuberculosis* which is homologous to the heat shock proteins groES from *E.coli* and the htpA gene product of *Coxiella burneti*", Nucleic Acids Research, vol. 16, No. 18 p. 9047, (1988), XP-001074008.
M. Bassan, et al., "The identification of secreted heat shock 60 -like protein from rat glial cells and a human neuroblastoma cell line", Neuroscience Letters 250, 37-40, (1998).
J. T. Beech, et al., "CD4+ Th2 Cells Specific for Mycobacterial 65-kilodalton Heat Shock Protein Protect Against Pristane-Induced Arthritis", The Journal of Immunology, 159, 3692-3697, (1997).
K. Bethke, et al., "Different Efficiency of Heat Shock Proteins (HSP) to Activate Human Monocytes and Dendritic Cells: Superiority of HSP60", The Journal of Immunology, 169, 6141-6148, (2002).
V. L. D. Bonato, et al, "Identification and Characterization of Protective T Cells in hsp65 DNA-Vaccinated and *Mycobacterium tuberculosis*-Infected Mice", Infection and Immunity, vol. 66, No. 1, pp. 169-175, Jan. 1998.
A. C. Cavanagh, "Identification of early pregnancy factor as chaperonin 10: implications for understanding its role", Reviews of Reproduction, 1, 28-32, (1996).
H. Chiu, et al., "Differential Induction of Heme Oxygenase- 1 in Macrophages and Hepatocytes during Acetaminophen-Induced Hepatotoxicity in the Rat: Effects of Hemin and Biliverdin", Toxicology and Applied Pharmacology 181, 106-115, (2002).
A. R. M. Coates, et al., "Chaperonins in Health and Disease", Annals of NY Academy of Sciences, 851, 48-52, (1998).
A. R. M. Coates, et al., "The Unfolding Story of the Chaperonins", Biotechnology and Genetic Engineering Reviews, vol. 16, pp. 393-405, Apr. 1999.
A. R. M. Coates, "Immunological Aspects of Chaperonins", The Chaperonins, Academic Press 267-296, (1996).
I. R. Cohen, "Peptide therapy for Type I diabetes: the immunological homunculus and the rationale for vaccination", Diabetologia, 45, 1468-1474, (2002).
N. Cranswick, et al., "Paracetamol Efficacy and Safety in Children: the First 40 Years", American Journal of Therapeutics, 7, 135-141, (2000).
H. L. F. Currey, et al., "Suppression of Adjuvant Disease in the Rat by Heterologous Antilymphocyte Globulin", J. Exp. Med., 127, 185-203, (1968).

(Continued)

*Primary Examiner*—Rodney P. Swartz
(74) *Attorney, Agent, or Firm*—Sughrue Mion, PLLC

(57) ABSTRACT

The present invention concerns the use of a heat shock polypeptide and/or an encoding nucleic acid sequence in the manufacture of a medicament for use in the relief of pain. In particular the invention concerns the use of chaperonin. The invention further provides methods of relieving pain medicaments containing the heat shock polypeptides.

20 Claims, 11 Drawing Sheets

OTHER PUBLICATIONS

Figure 4:
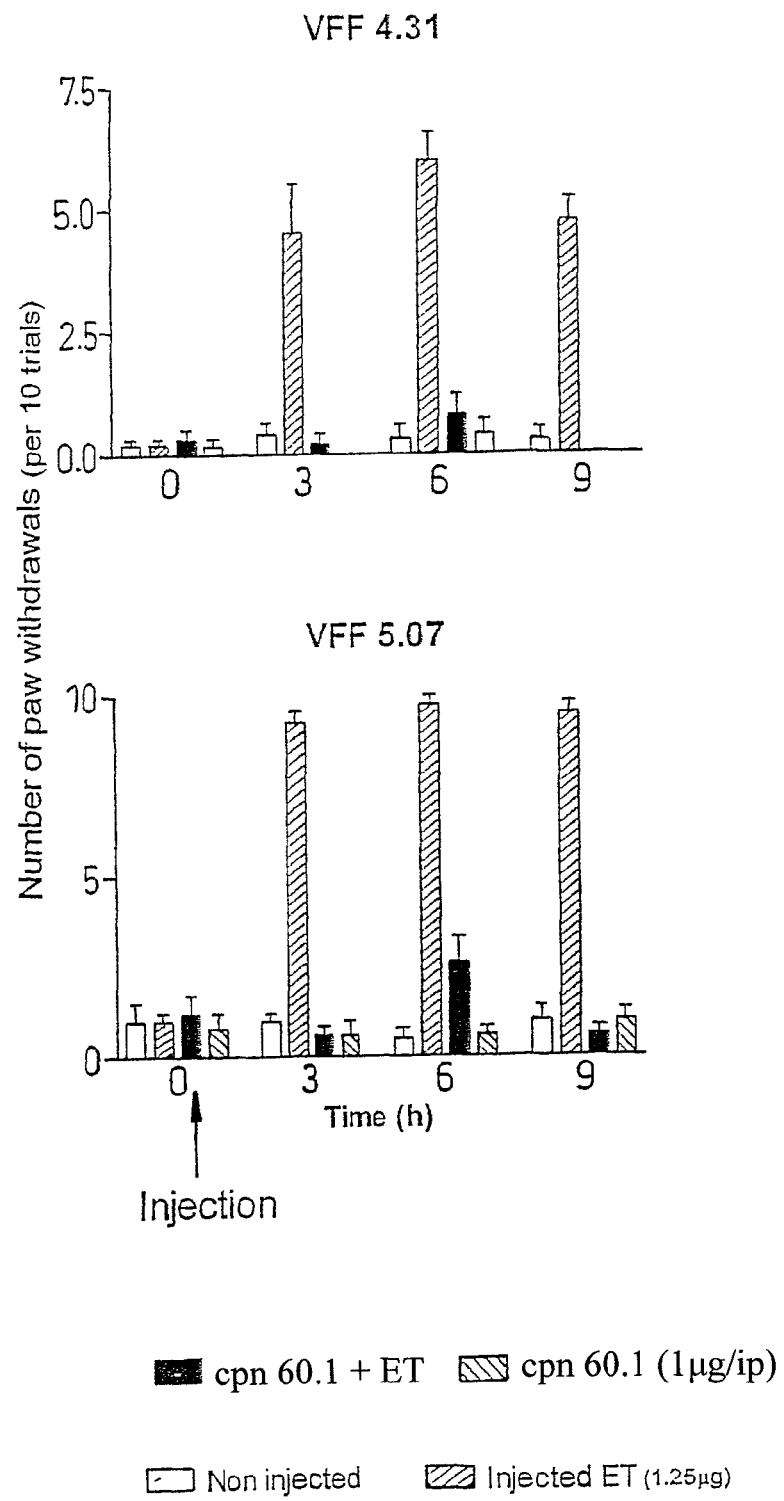

D. Elias, "Induction and therapy of autoimmune diabetes in the non-obese diabetic (NOD/Lt) mouse by a 65-kDa heat shock protein", Proc. Natl. Acad. Sci. USA, vol. 87, pp. 1576-1580, Feb. 1990.
C. El-Khoury, et al., "Attenuation of Neuropathic Pain by Segmental and Supraspinal Activation of the Dorsal Column System in Awake Rats", Neuroscience vol. 112, No. 3, pp. 541-553, (2002).
S. B. Flohé, et al., "Human Heat Shock Protein 60 Induces Maturation of Dendritic Cells Versus a Th1-Promoting Phenotype", The Journal of Immunology, 170, 2340-2348, (2003).
J. S. Friedland, et al., "Mycobacterial 65-kD heat shock protein induces release of proinflammatory cytokines from human monocytic cells", Clin Exp Immunol, 91, 58-62, (1993).
A. Frisk, et al., "GroEL Heat Shock Protein of *Haemophilus ducreyi*: Association with Cell Surface and Capacity To Bind to Eukaryotic Cells", Infection and Immunity, vol. 66, No. 3, pp. 1252-1257, Mar. 1998.
G. Furness, "A breath of fresh air", Scrip Magazine, Pharmaceutical issues in perspective, pp. 10-13, Nov. 2004.
S. E. Girardin, et al., "Intracellular vs extracellular recognition of pathogens—common concepts in mammals and flies", Trends in Microbiology, vol. 10, No. 4, pp. 193-199, Apr. 2002.
A. P. Gobert, et al., "*Helicobacter pylori* Heat Shock Protein 60 Mediates Interleukin-6 Production by Macrophages via a Toll-like Receptor (TLR)-2-, TLR-4-, and Myeloid Differentiation Factor 88-independent Mechanism", The Journal of Biological Chemistry, vol. 279, No. 1 pp. 245-250, Jan. 2, 2004.
F. Goulhen, et al., "Subcellular Localization and Cytotoxic Activity of the GroEL-Like Protein Isolated from *Actinobacillus actinomycetemcomitans*", Infection and Immunity, vol. 66, No. 11, pp. 5307-5313, Nov. 1998.
C. Habich, et al., "Different heat shock protein 60 species share pro-inflammatory activity but not binding sites on macrophages", FEBS Letters, 533, 105-109, (2003).
B. Henderson, et al., "Molecular chaperones and disease", Inflammation Research, 45, (155-158), 1996.
W. S. Hills, "Areas of Emerging Interest in Analgesia: Cardiovascular Complications", American Journal of Therapeutics, 9, 259-269, (2002).
S. Jindal, "Heat Shock Proteins in Infections and Immunity", Heat Shock Proteins conference handout, Cambridge Center Marriott, Cambridge, MA, Sep. 29-30, 1994.
S. A. Kanaan, et al., "Endotoxin-induced local inflammation and hyperalgesia in rats and mice: a new model for inflammatory pain", Pain, 66, 373-379, (1996).
Kirby, et al., "Potent Bone-resorbing Mediator of *Actinobacillus actinomycetemcomitans* homologous to the Molecular Chaperone GroEL", J Clin Invest 96, 1185-1194, (1995).
A. Kol, et al., "Chlamydial Heat Shock Protein 60 Localizes in Human Atheroma and Regulates Macrophage Tumor Necrosis Factor-α and Matrix Metalloproteinase Expression", Circulation, 98, 300-307 (1998).
A. Kol, et al., "Chlamydial and human heat shock protein 60s activate human vascular endothelium, smooth muscle cells, and macrophages", The Journal of Clinical Investigation, vol. 103, No. 4, 571-577, Feb. 1999.
T. H. Kong, et al., "*Mycobacterium tuberculosis* expresses two chaperonin-60 homologs", Proc. Natl. Acad. Sci. USA, vol. 90, 2608-2612, Apr. 1993 Microbiology.
R. A. Laskey, et al., "Nucleosomes are assembled by an acidic protein which binds histones and transfers them to DNA", Nature, vol. 275, 416-420, Oct. 5, 1978.
J. Lewthwaite, et al., "*Rhizobium leguminosarum* chaperonin 60.3, but not chaperonin 60.1, induces cytokine production by human monocytes: activity is dependent on interaction with cell surface CD14", Cell Stress and Chaperonins, 7 (2) 130-136, (2002).
J. Lewthwaite, et al., "Circulating Human Heat Shock Protein 60 in the Plasma of British Civil Servants", Circulation, 106, 196-201, (2002).
J. Lewthwaite, et al., "*Mycobacterium tuberculosis* Chaperonin 60.1 Is a More Potent Cytokine Stimulator than Chaperonin 60.2 (Hsp 65) and Contains a CD14-Binding Domain", Infection and Immunity, vol. 69, No. 12, 7349-7355, Dec. 2001.
D. B. Lowrie, et al., "Therapy of tuberculosis in mice by DNA vaccination", Nature, vol. 400, 269-271, Jul. 15, 1999.
P. Matzinger, "An innate sense of danger", seminars in Immunology, vol. 10, 399-415, (1998).
R. Medzhitov, et al., "Innate Immunity: The Virtues of a Nonclonal System of Recognition", Cell, vol. 91, 295-298, Oct. 31, 1997.
S. Meghji, et al., "*Mycobacterium tuberculosis* Chaperonin 10 Stimulates Bone Resorption: A Potential Contributory Factor in Pott's Disease", J. Exp. Med., vol. 186, No. 8, 1241-1246, Oct. 20, 1997.
W. E. Peetermans, et al., Infection and Immunity, vol. 63, No. 9, 3454-3458, Sep. 1995.
J. H. L. Playfair, "Immunology at a Glance", Blackwell Scientific Publications, Ch. 27 & 30, (1979).
S. Ragno, et al., "A synthetic 10-kD heat shock protein (hsp10) from *Mycobacterium tuberculosis* modulates adjuvant arthritis", Clin Exp Immunol, 103, 384-390, (1996).
J. C. Ranford, et al., "Chaperonins are cell-signalling proteins: the unfolding biology of molecular chaperones", Expert Reviews in Molecular Medicine: http://www-ermm.cbcu.cam.ac.uk/0000201-5h.htm, Sep. 15, 2000.
N. A. Ranson, et al., "Review Article Chaperonins", Biochem. J., 333, 233-242, (1998), Great Britain.
I Raz, et al., "β-cell function in new-onset type 1 diabetes and immunomodulation with a heat-shock protein peptide (DiaPep277): a randomized, double-blind, phase II trial", The Lancet, vol. 358, 1749-1753, (2001).
K. Reddi, et al., "The *Escherichia coli* Chaperonin 60 (groEL) Is a Potent Stimulator of Osteoclast Formation", Journal of Bone and Mineral Research, vol. 13., No. 8, 1260-1266, (1998).
Y. Rha, et al., "Effect of Microbial Heat Shock Proteins on Airway Inflammation and Hyperresponsiveness", The Journal of Immunology, 169, 5300-5307, (2002).
S. Sasu, et al., "*Chlamydia pneumoniae* and Chlamydial Heat Shock Protein 60 Stimulate Proliferation of Human Vascular Smooth Muscle Cells via Toll-Like Receptor 4 and p44/p42 Mitogen-Activated Protein Kinase Activation", Circulation Research, 89, 244-250, (2001).
S. Steinfeld, et al., "Results from a patient survey to assess gastrointestinal burden of non-steroidal anti-inflammatory drug therapy contrasted with a review of data from EVA to determine satisfaction with rofecoxib", Rheumatology, 41 (suppl. 1), 23-27, (2002.
P. Tabona, et al., "Homogeneous *Escherichia coli* Chaperonin 60 Induces IL-1β and IL-6 Gene Expression in Human Monocytes by a Mechanism Independent of Protein Conformation", The Journal of Immunology, 161, 1414-1421, (1998).
K. Takahashi, et al., "Analysis of heat shock proteins and cytokines expressed during early stages of osteoarthritis in a mouse model", Osteoarthritis and Cartilage, 5, 321-329, (1997).
S. J. Thompson, et al., "An Immunodominant Epitope from Mycobacterial 65-kDa Heat Shock Protein Protects Against Pristane-Induced Arthritis", The Journal of Immunology, 160, 4628-4634, (1998).
J. D. Thompson, "Clustal W: improving the sensitivity of progressive multiple sequence alignment through sequence weighting, position-specific gap penalties and weight matrix choice", Nucleic Acids Research, vol. 22, No. 22, 4673-4680, (1994).
W. van Eden, et al., "Cloning of the mycobacterial epitope recognized by T lymphocytes in adjuvant arthritis", Nature vol. 331, 171-173, Jan. 14, 1988.
E. M. E. Verdegaal, et al., "Heat Shock Protein 65 Induces CD62e, CD106, and CD54 on Cultured Human Endothelial Cells and Increases Their Adhesiveness for Monocytes and Granulocytes", The Journal of Immunology, 157, 369-376, (1996).
V. R. Windrow, et al., "Arthritogenic potential of the 65 kDa stress protein—an experimental model", Annals of the Rheumatic Diseases, 53, 197-201, (1994).
N. Yoshida, et al., "Chaperonin turned insect toxin", Nature, 411, p. 44, (2001).
U. Zügel, et al., "Role of Heat Shock Proteins in Protection from and Pathogenesis of Infectious Diseases", Clinical Microbiology Reviews, vol. 12, No. 1, p. 19-39, Jan. 1999.
XP-002203460, EBI accession No. Q59573; 60 kDa chaperonin.

MT Cpn 60.1

```
  1  ATGAGCAAGCTGATCGAATACGACGAAACCGCGCGTCGCGCCATGGAGGTCGGCATGGAC   60
     M  S  K  L  I  E  Y  D  E  T  A  R  R  A  M  E  V  G  M  D

61  AAGCTGGCCGACACCGTGCGGGTGACGCTGGGGCCGCGCGGCCGGCATGTGGTGCTGGCC  120
     K  L  A  D  T  V  R  V  T  L  G  P  R  G  R  H  V  V  L  A

121  AAGGCGTTTGGCGGACCCACGGTTACCAACGACGGCGTCACGGTGGCACGTGAGATCGAG  180
     K  A  F  G  G  P  T  V  T  N  D  G  V  T  V  A  R  E  I  E

181  CTGGAAGATCCGTTTGAAGACTTGGGCGCCCAGCTGGTGAAGTCGGTGGCCACCAAGACC  240
     L  E  D  P  F  E  D  L  G  A  Q  L  V  K  S  V  A  T  K  T

241  AACGATGTGGCCGGTGACGGCACCACCACCGCAACCATCTTGGCGCAGGCACTGATCAAG  300
     N  D  V  A  G  D  G  T  T  T  A  T  I  L  A  Q  A  L  I  K
                             n
301  GGCGGCCTGAGGCTAGTGGCCGCCGGCGTCAACCCGATCGCGCTCGGCGTGGGAATCGGC  360
     G  G  L  R  L  V  A  A  G  V  N  P  I  A  L  G  V  G  I  G

361  AAGGCCGCCGACGCGGTATCCGAGGCGCTGCTGGCATCGGCCACGCCGGTGTCCGGCAAG  420
     K  A  A  D  A  V  S  E  A  L  L  A  S  A  T  P  V  S  G  K

421  ACCGGCATCGCGCAGGTGGCGACGGTGTCCTCGCGCGACGAGCAGATCGGTGACCTGGTT  480
     T  G  I  A  Q  V  A  T  V  S  S  R  D  E  Q  I  G  D  L  V

481  GGCGAAGCGATGAGCAAGGTCGGCCACGACGGCGTGGTCAGCGTCGAAGAATCCTCGACG  540
     G  E  A  M  S  K  V  G  H  D  G  V  V  S  V  E  E  S  S  T

541  CTGGGCACCGAGTTGGAGTTCACCGAGGGTATCGGCTTCGACAAGGGCTTCTTGTCGGCA  600
     L  G  T  E  L  E  F  T  E  G  I  G  F  D  K  G  F  L  S  A

601  TACTTCGTTACCGACTTCGATAACCAGCAGGCGGTGCTCGAGGACGCGTTGATCCTGCTG  660
     Y  F  V  T  D  F  D  N  Q  Q  A  V  L  E  D  A  L  I  L  L

661  CACCAAGACAAGATCAGCTCGCTTCCCGATCTGTTGCCATTGCTGGAAAAGGTTGCAGGA  720
     H  Q  D  K  I  S  S  L  P  D  L  L  P  L  L  E  K  V  A  G

721  ACGGGTAAGCCACTACTGATCGTGGCTGAAGACGTGGAGGGCGAAGCGTTGGCGACGCTG  780
     T  G  K  P  L  L  I  V  A  E  D  V  E  G  E  A  L  A  T  L

781  GTCGTCAACGCGATTCGCAAGACGTTGAAAGCGGTCGCGGTCAAGGGGCCGTACTTCGGT  840
     V  V  N  A  I  R  K  T  L  K  A  V  A  V  K  G  P  Y  F  G

841  GACCGCCGTAAGGCGTTCCTTGAGGACCTGGCGGTGGTGACGGGTGGCCAGGTGGTCAAC  900
     D  R  R  K  A  F  L  E  D  L  A  V  V  T  G  G  Q  V  V  N
```

Fig. 1 (Part 1 of 2)

```
 901   CCCGACGCCGGCATGGTGCTGCGCGAGGTGGGCTTGGAGGTGCTGGGCTCGGCCCGACGC   960
       P  D  A  G  M  V  L  R  E  V  G  L  E  V  L  G  S  A  R  R

961   GTGGTGGTCAGCAAGGACGACACGGTCATTGTCGACGGCGGCGGCACCGCAGAAGCGGTG  1020
       V  V  V  S  K  D  D  T  V  I  V  D  G  G  G  T  A  E  A  V

1021   GCCAACCGGGCGAAGCACTTGCGTGCCGAGATCGACAAGAGCGATTCGGATTGGGATCGG  1080
       A  N  R  A  K  H  L  R  A  E  I  D  K  S  D  S  D  W  D  R

1081   GAAAAGCTTGGCGAGCGGCTGGCCAAACTGGCCGGCGGGGTTGCTGTCATCAAGGTGGGT  1140
       E  K  L  G  E  R  L  A  K  L  A  G  G  V  A  V  I  K  V  G

1141   GCCGCCACCGAGACCGCACTCAAGGAGCGCAAGGAAAGCGTCGAGGATGCGGTCGCGGCC  1200
       A  A  T  E  T  A  L  K  E  R  K  E  S  V  E  D  A  V  A  A

1201   GCCAAGGCCGCGGTCGAGGAGGGCATCGTCCCTGGTGGGGGAGCCTCGCTCATCCACCAG  1260
       A  K  A  A  V  E  E  G  I  V  P  G  G  G  A  S  L  I  H  Q

1261   GCCCGCAAGGCGCTGACCGAACTGCGTGCGTCGCTGACCGGTGACGAGGTCCTCGGTGTC  1320
       A  R  K  A  L  T  E  L  R  A  S  L  T  G  D  E  V  L  G  V

1321   GACGTGTTCTCCGAAGCCCTTGCCGCGCCGTTGTTCTGGATCGCCGCCAACGCTGGCTTG  1380
       D  V  F  S  E  A  L  A  A  P  L  F  W  I  A  A  N  A  G  L

1381   GACGGCTCGGTGGTGGTCAACAAGGTCAGCGAGCTACCCGCCGGGCATGGGCTGAACGTG  1440
       D  G  S  V  V  V  N  K  V  S  E  L  P  A  G  H  G  L  N  V

1441   AACACCCTGAGCTATGGTGACTTGGCCGCTGACGGCGTCATCGACCCGGTCAAGGTGACT  1500
       N  T  L  S  Y  G  D  L  A  A  D  G  V  I  D  P  V  K  V  T

1501   AGGTCGGCGGTGTTGAACGCGTCATCGGTTGCCCGGATGGTACTCACCACCGAGACGGTC  1560
       R  S  A  V  L  N  A  S  S  V  A  R  M  V  L  T  T  E  T  V

1561   GTGGTCGACAAGCCGGCCAAGGCAGAAGATCACGACCATCACCACGGGCACGCGCACTGA  1620
       V  V  D  K  P  A  K  A  E  D  H  D  H  H  H  G  H  A  H  *
```

Fig. 1 *(Part 2 of 2)*

Mt Cpn60.2

```
  1  ATGGCCAAGACAATTGCGTACGACGAAGAGGCCCGTCGCGGCCTCGAGCGGGGCTTGAAC   60
     M  A  K  T  I  A  Y  D  E  E  A  R  R  G  L  E  R  G  L  N

61  GCCCTCGCCGATGCGGTAAAGGTGACATTGGGCCCCAAGGGCCGCAACGTCGTCCTGGAA  120
     A  L  A  D  A  V  K  V  T  L  G  P  K  G  R  N  V  V  L  E

121  AAGAAGTGGGGTGCCCCCACGATCACCAACGATGGTGTGTCCATCGCCAAGGAGATCGAG  180
     K  K  W  G  A  P  T  I  T  N  D  G  V  S  I  A  K  E  I  E

181  CTGGAGGATCCGTACGAGAAGATCGGCGCCGAGCTGGTCAAAGAGGTAGCCAAGAAGACC  240
     L  E  D  P  Y  E  K  I  G  A  E  L  V  K  E  V  A  K  K  T

241  GATGACGTCGCCGGTGACGGCACCACGACGGCCACCGTGCTGGCCCAGGCGTTGGTTCGC  300
     D  D  V  A  G  D  G  T  T  T  A  T  V  L  A  Q  A  L  V  R

301  GAGGGCCTGCGCAACGTCGCGGCCGGCGCCAACCCGCTCGGTCTCAAACGCGGCATCGAA  360
     E  G  L  R  N  V  A  A  G  A  N  P  L  G  L  K  R  G  I  E

361  AAGGCCGTGGAGAAGGTCACCGAGACCCTGCTCAAGGGCGCCAAGGAGGTCGAGACCAAG  420
     K  A  V  E  K  V  T  E  T  L  L  K  G  A  K  E  V  E  T  K

421  GAGCAGATTGCGGCCACCGCAGCGATTTCGGCGGGTGACCAGTCCATCGGTGACCTGATC  480
     E  Q  I  A  A  T  A  A  I  S  A  G  D  Q  S  I  G  D  L  I

481  GCCGAGGCGATGGACAAGGTGGGCAACGAGGGCGTCATCACCGTCGAGGAGTCCAACACC  540
     A  E  A  M  D  K  V  G  N  E  G  V  I  T  V  E  E  S  N  T

541  TTTGGGCTGCAGCTCGAGCTCACCGAGGGTATGCGGTTCGACAAGGGCTACATCTCGGGG  600
     F  G  L  Q  L  E  L  T  E  G  M  R  F  D  K  G  Y  I  S  G

601  TACTTCGTGACCGACCCGGAGCGTCAGGAGGCGGTCCTGGAGGACCCCTACATCCTGCTG  660
     Y  F  V  T  D  P  E  R  Q  E  A  V  L  E  D  P  Y  I  L  L

661  GTCAGCTCCAAGGTGTCCACTGTCAAGGATCTGCTGCCGCTGCTCGAGAAGGTCATCGGA  720
     V  S  S  K  V  S  T  V  K  D  L  L  P  L  L  E  K  V  I  G

721  GCCGGTAAGCCGCTGCTGATCATCGCCGAGGACGTCGAGGGCGAGGCGCTGTCCACCCTG  780
     A  G  K  P  L  L  I  I  A  E  D  V  E  G  E  A  L  S  T  L

781  GTCGTCAACAAGATCCGCGGCACCTTCAAGTCGGTGGCGGTCAAGGCTCCCGGCTTCGGC  840
     V  V  N  K  I  R  G  T  F  K  S  V  A  V  K  A  P  G  F  G
```

*Fig. 2 (Part 1 of 2)*

```
841  GACCGCCGCAAGGCGATGCTGCAGGATATGGCCATTCTCACCGGTGGTCAGGTGATCAGC  900
      D   R   R   K   A   M   L   Q   D   M   A   I   L   T   G   G   Q   V   I   S

901  GAAGAGGTCGGCCTGACGCTGGAGAACGCCGACCTGTCGCTGCTAGGCAAGGCCCGCAAG  960
      E   E   V   G   L   T   L   E   N   A   D   L   S   L   L   G   K   A   R   K

961  GTCGTGGTCACCAAGGACGAGACCACCATCGTCGAGGGCGCCGGTGACACCGACGCCATC 1020
      V   V   V   T   K   D   E   T   T   I   V   E   G   A   G   D   T   D   A   I

1021 GCCGGACGAGTGGCCCAGATCCGCCAGGAGATCGAGAACAGCGACTCCGACTACGACCGT 1080
      A   G   R   V   A   Q   I   R   Q   E   I   E   N   S   D   S   D   Y   D   R

1081 GAGAAGCTGCAGGAGCGGCTGGCCAAGCTGGCCGGTGGTGTCGCGGTGATCAAGGCCGGT 1140
      E   K   L   Q   E   R   L   A   K   L   A   G   G   V   A   V   I   K   A   G

1141 GCCGCCACCGAGGTCGAACTCAAGGAGCGCAAGCACCGCATCGAGGATGCGGTTCGCAAT 1200
      A   A   T   E   V   E   L   K   E   R   K   H   R   I   E   D   A   V   R   N

1201 GCCAAGGCCGCCGTCGAGGAGGGCATCGTCGCCGGTGGGGGTGTGACGCTGTTGCAAGCG 1260
      A   K   A   A   V   E   E   G   I   V   A   G   G   G   V   T   L   L   Q   A

1261 GCCCCGACCCTGGACGAGCTGAAGCTCGAAGGCGACGAGGCGACCGGCGCCAACATCGTG 1320
      A   P   T   L   D   E   L   K   L   E   G   D   E   A   T   G   A   N   I   V

1321 AAGGTGGCGCTGGAGGCCCCGCTGAAGCAGATCGCCTTCAACTCCGGGCTGGAGCCGGGC 1380
      K   V   A   L   E   A   P   L   K   Q   I   A   F   N   S   G   L   E   P   G

1381 GTGGTGGCCGAGAAGGTGCGCAACCTGCCGGCTGGCCACGGACTGAACGCTCAGACCGGT 1440
      V   V   A   E   K   V   R   N   L   P   A   G   H   G   L   N   Q   T   G

1441 GTCTACGAGGATCTGCTCGCTGCCGGCGTTGCTGACCCGGTCAAGGTGACCCGTTCGGCG 1500
      V   Y   E   D   L   L   A   A   G   V   A   D   P   V   K   V   T   R   S   A

1501 CTGCAGAATGCGGCGTCCATCGCGGGGCTGTTCCTGACCACCGAGGCCGTCGTTGCCGAC 1560
      L   Q   N   A   A   S   I   A   G   L   F   L   T   T   E   A   V   V   A   D

1561 AAGCCGGAAAAGGAGAAGGCTTCCGTTCCCGGTGGCGGCGACATGGGTGGCATGGATTTC 1620
      K   P   E   K   E   K   A   S   V   P   G   G   G   D   M   G   G   M   D   F

1621 TGA                                                           1623
      *
```

Fig. 2 *(Part 2 of 2)*

MT Cpn 10

```
  1  GTGGCGAAGGTGAACATCAAGCCACTCGAGGACAAGATTCTCGTGCAGGCCAACGAGGCC   60
      M  A  K  V  N  I  K  P  L  E  D  K  I  L  V  Q  A  N  E  A
 61  GAGACCACGACCGCGTCCGGTCTGGTCATTCCTGACACCGCCAAGGAGAAGCCGCAGGAG  120
      E  T  T  T  A  S  G  L  V  I  P  D  T  A  K  E  K  P  Q  E
121  GGCACCGTCGTTGCCGTCGGCCCTGGCCGGTGGGACGAGGACGGCGAGAAGCGGATCCCG  180
      G  T  V  V  A  V  G  P  G  R  W  D  E  D  G  E  K  R  I  P
181  CTGGACGTTGCGGAGGGTGACACCGTCATCTACAGCAAGTACGGCGGCACCGAGATCAAG  240
      L  D  V  A  E  G  D  T  V  I  Y  S  K  Y  G  G  T  E  I  K
241  TACAACGGCGAGGAATACCTGATCCTGTCGGCACGCGACGTGCTGGCCGTCGTTTCCAAG  300
      Y  N  G  E  E  Y  L  I  L  S  A  R  D  V  L  A  V  V  S  K
301  TAG                                                           360
      *
```

*Fig. 3*

```
                            SEQUENCE LISTING

<160> NUMBER OF SEQ ID NOS: 6

<210> SEQ ID NO 1
<211> LENGTH: 1620
<212> TYPE: DNA
<213> ORGANISM: Mycobacterium tuberculosis

<400> SEQUENCE: 1
atgagcaagc tgatcgaata cgacgaaacc gcgcgtcgcg ccatggaggt cggcatggac      60
aagctggccg acaccgtgcg ggtgacgctg gggccgcgcg gccggcatgt ggtgctggcc     120
aaggcgtttg gcggacccac ggttaccaac gacggcgtca cggtggcacg tgagatcgag     180
ctggaagatc cgtttgaaga cttgggcgcc cagctggtga agtcggtggc caccaagacc     240
aacgatgtgc ccggtgacgg caccaccacc gcaaccatct ggcgcaggc actgatcaag      300 ggcggcctga ggctagtggc cgccggcgtc aacccgatcg cgctcggcgt gggaatcggc     360
aaggccgccg acgcggtatc cgaggcgctg ctggcatcgg ccacgccggt gtccggcaag     420
accggcatcg cgcaggtggc gacggtgtcc tcgcgcgacg agcagatcgg tgacctggtt     480
ggcgaagcga tgagcaaggt cggccacgac ggcgtggtca gcgtcgaaga tcctcgacg     540 ctgggcaccg agttggagtt caccgagggt atcggcttcg acaagggctt cttgtcggca     600
tacttcgtta ccgacttcga taaccagcag gcggtgctcg aggacgcgtt gatcctgctg     660
caccaagaca agatcagctc gcttcccgat ctgttgccat tgctggaaaa ggttgcagga     720
acgggtaagc cactactgat cgtggctgaa gacgtggagg cgaagcgtt ggcgacgctg      780 gtcgtcaacg cgattcgcaa gacgttgaaa gcggtcgcgg tcaaggggcc gtacttcggt     840
gaccgccgta aggcgttcct tgaggacctg gcggtggtga cgggtggcca ggtggtcaac     900
cccgacgccg gcatggtgct gcgcgaggtg ggcttggagg tgctgggctc ggcccgacgc     960
gtggtggtca gcaaggacga cacggtcatt gtcgacggcg gcggcaccgc agaagcggtg    1020
gccaaccggg cgaagcactt gcgtgccgag atcgacaaga gcgattcgga ttgggatcgg    1080
gaaaagcttg gcgagcggct ggccaaactg gccggcgggg ttgctgtcat caaggtgggt    1140
gccgccaccg agaccgcact caaggagcgc aaggaaagcg tcgaggatgc ggtcgcggcc    1200
gccaaggccg cggtcgagga gggcatcgtc cctggtgggg gagcctcgct catccaccag    1260
gcccgcaagg cgctgaccga actgcgtgcg tcgctgaccg gtgacgaggt cctcggtgtc    1320
gacgtgttct ccgaagccct tgccgcgccg ttgttctgga tcgccgccaa cgctggcttg    1380
gacggctcgg tggtggtcaa caaggtcagc gagctacccg ccgggcatgg gctgaacgtg    1440
aacaccctga gctatggtga cttggccgct gacggcgtca tcgacccggt caaggtgact    1500
aggtcggcgg tgttgaacgc gtcatcggtt gcccggatgg tactcaccac cgagacggtc    1560
gtggtcgaca agccggccaa ggcagaagat cacgaccatc accacgggca cgcgcactga    1620

<210> SEQ ID NO 2
<211> LENGTH: 539
<212> TYPE: PRT
<213> ORGANISM: Mycobacterium tuberculosis
```

```
<400> SEQUENCE: 2

Met Ser Lys Leu Ile Glu Tyr Asp Glu Thr Ala Arg Arg Ala Met Glu
1               5                   10                  15

Val Gly Met Asp Lys Leu Ala Asp Thr Val Arg Val Thr Leu Gly Pro
            20                  25                  30

Arg Gly Arg His Val Val Leu Ala Lys Ala Phe Gly Gly Pro Thr Val
        35                  40                  45

Thr Asn Asp Gly Val Thr Val Ala Arg Glu Ile Glu Leu Glu Asp Pro
    50                  55                  60

Phe Glu Asp Leu Gly Ala Gln Leu Val Lys Ser Val Ala Thr Lys Thr
65                  70                  75                  80

Asn Asp Val Ala Gly Asp Gly Thr Thr Thr Ala Thr Ile Leu Ala Gln
                85                  90                  95

Ala Leu Ile Lys Gly Gly Leu Arg Leu Val Ala Ala Gly Val Asn Pro
            100                 105                 110

Ile Ala Leu Gly Val Gly Ile Gly Lys Ala Ala Asp Ala Val Ser Glu
        115                 120                 125

Ala Leu Leu Ala Ser Ala Thr Pro Val Ser Gly Lys Thr Gly Ile Ala
    130                 135                 140

Gln Val Ala Thr Val Ser Ser Arg Asp Glu Gln Ile Gly Asp Leu Val
145                 150                 155                 160

Gly Glu Ala Met Ser Lys Val Gly His Asp Gly Val Val Ser Val Glu
                165                 170                 175

Glu Ser Ser Thr Leu Gly Thr Glu Leu Glu Phe Thr Glu Gly Ile Gly
            180                 185                 190

Phe Asp Lys Gly Phe Leu Ser Ala Tyr Phe Val Thr Asp Phe Asp Asn
        195                 200                 205

Gln Gln Ala Val Leu Glu Asp Ala Leu Ile Leu Leu His Gln Asp Lys
    210                 215                 220

Ile Ser Ser Leu Pro Asp Leu Leu Pro Leu Leu Glu Lys Val Ala Gly
225                 230                 235                 240

Thr Gly Lys Pro Leu Leu Ile Val Ala Glu Asp Val Glu Gly Glu Ala
                245                 250                 255

Leu Ala Thr Leu Val Val Asn Ala Ile Arg Lys Thr Leu Lys Ala Val
            260                 265                 270

Ala Val Lys Gly Pro Tyr Phe Gly Asp Arg Arg Lys Ala Phe Leu Glu
        275                 280                 285

Asp Leu Ala Val Val Thr Gly Gly Gln Val Val Asn Pro Asp Ala Gly
    290                 295                 300

Met Val Leu Arg Glu Val Gly Leu Glu Val Leu Gly Ser Ala Arg Arg
305                 310                 315                 320

Val Val Val Ser Lys Asp Asp Thr Val Ile Val Asp Gly Gly Gly Thr
                325                 330                 335

Ala Glu Ala Val Ala Asn Arg Ala Lys His Leu Arg Ala Glu Ile Asp
            340                 345                 350

Lys Ser Asp Ser Asp Trp Asp Arg Glu Lys Leu Gly Glu Arg Leu Ala
        355                 360                 365

Lys Leu Ala Gly Gly Val Ala Val Ile Lys Val Gly Ala Ala Thr Glu
    370                 375                 380

Thr Ala Leu Lys Glu Arg Lys Glu Ser Val Glu Asp Ala Val Ala Ala
385                 390                 395                 400

Ala Lys Ala Ala Val Glu Glu Gly Ile Val Pro Gly Gly Gly Ala Ser
                405                 410                 415
```

```
Leu Ile His Gln Ala Arg Lys Ala Leu Thr Glu Leu Arg Ala Ser Leu
            420                 425                 430

Thr Gly Asp Glu Val Leu Gly Val Asp Val Phe Ser Glu Ala Leu Ala
        435                 440                 445

Ala Pro Leu Phe Trp Ile Ala Asn Ala Gly Leu Asp Gly Ser Val
    450                 455                 460

Val Val Asn Lys Val Ser Glu Leu Pro Ala Gly His Gly Leu Asn Val
465                 470                 475                 480

Asn Thr Leu Ser Tyr Gly Asp Leu Ala Ala Asp Gly Val Ile Asp Pro
                485                 490                 495

Val Lys Val Thr Arg Ser Ala Val Leu Asn Ala Ser Ser Val Ala Arg
            500                 505                 510

Met Val Leu Thr Thr Glu Thr Val Val Val Asp Lys Pro Ala Lys Ala
        515                 520                 525

Glu Asp His Asp His His His Gly His Ala His
    530                 535
```

<210> SEQ ID NO 3
<211> LENGTH: 1623
<212> TYPE: DNA
<213> ORGANISM: Mycobacterium tuberculosis

<400> SEQUENCE: 3

```
atggccaaga caattgcgta cgacgaagag gcccgtcgcg gcctcgagcg gggcttgaac      60
gccctcgccg atgcggtaaa ggtgacattg gccccaagg ccgcaacgt cgtcctggaa       120 aagaagtggg gtgccccac gatcaccaac gatggtgtgt ccatcgccaa ggagatcgag       180
ctggaggatc cgtacgagaa gatcggcgcc gagctggtca agaggtagc caagaagacc       240 gatgacgtcg ccggtgacgg caccacgacg gccaccgtgc tgcccaggc gttggttcgc      300 gagggcctgc gcaacgtcgc ggccggcgcc aacccgctcg gtctcaaacg cggcatcgaa      360
aaggccgtgg agaaggtcac cgagaccctg ctcaagggcg ccaaggaggt cgagaccaag      420
gagcagattg cggccaccgc agcgatttcg gcgggtgacc agtccatcgg tgacctgatc      480
gccgaggcga tggacaaggt gggcaacgag ggcgtcatca ccgtcgagga gtccaacacc      540
tttgggctgc agctcgagct caccgagggt atgcggttcg acaagggcta catctcgggg      600
tacttcgtga ccgacccgga cgtcaggag gcggtcctgg aggacccta catcctgctg       660 gtcagctcca aggtgtccac tgtcaaggat ctgctgccgc tgctcgagaa ggtcatcgga      720
gccggtaagc cgctgctgat catcgccgag gacgtcgagg gcgaggcgct gtccaccctg      780
gtcgtcaaca agatccgcgg caccttcaag tcggtggcgg tcaaggctcc cggcttcggc      840
gaccgccgca aggcgatgct gcaggatatg gccattctca ccggtggtca ggtgatcagc      900
gaagaggtcg gcctgacgct ggagaacgcc gacctgtcgc tgctaggcaa ggcccgcaag      960
gtcgtggtca ccaaggacga gaccaccatc gtcgagggcg ccggtgacac cgacgccatc     1020
gccggacgag tggcccagat ccgccaggag atcgagaaca gcgactccga ctacgaccgt     1080
gagaagctgc aggagcggct ggccaagctg gccggtggtg tcgcggtgat caaggccggt     1140
gccgccaccg aggtcgaact caaggagcgc aagcaccgca tcgaggatgc ggttcgcaat     1200
gccaaggccg ccgtcgagga gggcatcgtc gccggtgggg tgtgtgacgct gttgcaagcg     1260 gccccgaccc tggacgagct gaagctcgaa ggcgacgagg cgaccggcgc caacatcgtg     1320
aaggtggcgc tggaggcccc gctgaagcag atcgccttca actccgggct ggagccgggc     1380
gtggtggccg agaaggtgcg caacctgccg gctggccacg gactgaacgc tcagaccggt     1440
```

-continued

```
gtctacgagg atctgctcgc tgccggcgtt gctgacccgg tcaaggtgac ccgttcggcg    1500
ctgcagaatg cggcgtccat cgcggggctg ttcctgacca ccgaggccgt cgttgccgac    1560
aagccggaaa aggagaaggc ttccgttccc ggtggcggcg acatgggtgg catggatttc    1620
tga                                                                  1623
```

<210> SEQ ID NO 4
<211> LENGTH: 364
<212> TYPE: PRT
<213> ORGANISM: Mycobacterium tuberculosis

<400> SEQUENCE: 4

```
Met Ala Lys Thr Ala Tyr Asp Ala Arg Arg Gly Arg Gly Asn Ala Ala
1               5                   10                  15

Asp Ala Val Lys Val Thr Gly Lys Gly Arg Asn Val Val Lys Lys Trp
            20                  25                  30

Gly Ala Thr Thr Asn Asp Gly Val Ser Ala Lys Asp Tyr Lys Gly Ala
        35                  40                  45

Val Lys Val Ala Lys Lys Thr Asp Asp Val Ala Gly Asp Gly Thr Thr
    50                  55                  60

Thr Ala Thr Val Ala Ala Val Arg Gly Arg Asn Val Ala Ala Gly Ala
65                  70                  75                  80

Asn Gly Lys Arg Gly Lys Ala Val Lys Val Thr Thr Lys Gly Ala Lys
                85                  90                  95

Val Thr Lys Ala Ala Thr Ala Ala Ser Ala Gly Asp Ser Gly Asp Ala
            100                 105                 110

Ala Met Asp Lys Val Gly Asn Gly Val Thr Val Ser Asn Thr Gly Thr
        115                 120                 125

Gly Met Arg Asp Lys Gly Tyr Ser Gly Tyr Val Thr Asp Arg Ala Val
    130                 135                 140

Asp Tyr Val Ser Ser Lys Val Ser Thr Val Lys Asp Lys Val Gly Ala
145                 150                 155                 160

Gly Lys Ala Asp Val Gly Ala Ser Thr Val Asn Lys Arg Gly Thr
                165                 170                 175

Lys Ser Val Ala Val Lys Ala Gly Gly Asp Arg Arg Lys Ala Met Asp
            180                 185                 190

Met Ala Thr Gly Gly Val Ser Val Gly Thr Asn Ala Asp Ser Gly Lys
        195                 200                 205

Ala Arg Lys Val Val Val Thr Lys Asp Thr Thr Val Gly Ala Gly Asp
    210                 215                 220

Thr Asp Ala Ala Gly Arg Val Ala Arg Asn Ser Asp Ser Asp Tyr Asp
225                 230                 235                 240

Arg Lys Arg Ala Lys Ala Gly Gly Val Ala Val Lys Ala Gly Ala Ala
                245                 250                 255

Thr Val Lys Arg Lys His Arg Asp Ala Val Arg Asn Ala Lys Ala Ala
            260                 265                 270

Val Gly Val Ala Gly Gly Val Thr Ala Ala Thr Asp Lys Gly Asp
        275                 280                 285

Ala Thr Gly Ala Asn Val Lys Val Ala Ala Lys Ala Asn Ser Gly Gly
    290                 295                 300

Val Val Ala Lys Val Arg Asn Ala Gly His Gly Asn Ala Thr Gly Val
305                 310                 315                 320

Tyr Asp Ala Ala Gly Val Ala Asp Val Lys Val Thr Arg Ser Ala Asn
                325                 330                 335
```

-continued

```
Ala Ala Ser Ala Gly Thr Thr Ala Val Val Ala Asp Lys Lys Lys Ala
            340                 345                 350

Ser Val Gly Gly Gly Asp Met Gly Gly Met Asp Phe
        355                 360

<210> SEQ ID NO 5
<211> LENGTH: 303
<212> TYPE: DNA
<213> ORGANISM: Mycobacterium tuberculosis

<400> SEQUENCE: 5
gtggcgaagg tgaacatcaa gccactcgag gacaagattc tcgtgcaggc caacgaggcc         60
gagaccacga ccgcgtccgg tctggtcatt cctgacaccg ccaaggagaa gccgcaggag        120
ggcaccgtcg ttgccgtcgg ccctggccgg tgggacgagg acggcgagaa gcggatcccg        180
ctggacgttg cggagggtga caccgtcatc tacagcaagt acggcggcac cgagatcaag        240
tacaacggcg aggaatacct gatcctgtcg gcacgcgacg tgctggccgt cgtttccaag        300
tag                                                                     303

<210> SEQ ID NO 6
<211> LENGTH: 100
<212> TYPE: PRT
<213> ORGANISM: Mycobacterium tuberculosis

<400> SEQUENCE: 6

Met Ala Lys Val Asn Ile Lys Pro Leu Glu Asp Lys Ile Leu Val Gln
1               5                   10                  15

Ala Asn Glu Ala Glu Thr Thr Thr Ala Ser Gly Leu Val Ile Pro Asp
            20                  25                  30

Thr Ala Lys Glu Lys Pro Gln Glu Gly Thr Val Val Ala Val Gly Pro
        35                  40                  45

Gly Arg Trp Asp Glu Asp Gly Glu Lys Arg Ile Pro Leu Asp Val Ala
    50                  55                  60

Glu Gly Asp Thr Val Ile Tyr Ser Lys Tyr Gly Gly Thr Glu Ile Lys
65                  70                  75                  80

Tyr Asn Gly Glu Glu Tyr Leu Ile Leu Ser Ala Arg Asp Val Leu Ala
                85                  90                  95

Val Val Ser Lys
            100
```

PAIN RELIEF AGENTS

This application is a 371 of PCT/GB2003/004774, filed Nov. 5, 2003 and claims priority from GB 0226105.5 filed Nov. 8, 2002; the disclosure of which is incorporated herein by reference.

The present invention relates to pain relief agents and, in particular, pain relief agents which comprise one or more heat shock polypeptides.

Heat shock polypeptides are a family of molecules found in all organisms, whose function is to aid the biological processing and stability of biological molecules (Zugel & Kauffman (1999) *Role of heat shock polypeptides in protection from and pathogenesis of infectious diseases*. Clin. Microbiol. Rev. (12)1: 19-39; Ranford et al. (2000) *Chaperonins are cell signalling polypeptides:—the unfolding biology of molecular chaperones*. Exp. Rev. Mol. Med., 15 September, www.ermn.cbcu.cam.ac.uk/00002015h).

Heat shock polypeptides are located in every cellular compartment, and possess the ability to interact with a wide range of biological molecules. In particular, the heat shock polypeptides aid and influence polypeptide folding and polypeptide translocation at any time from assembly through to disassembly of the polypeptide and any complexes thereof. The helper nature of the heat shock polypeptides has led to them to also being known as molecular chaperones (Laskey et al. (1978) *Nucleosomes are assembled by an acidic polypeptide, which binds histones and transfers them to DNA*. Nature (275): 416-420).

Heat shock polypeptides are synthesized by cells in response to environmental stress, which includes, but is not limited to temperature changes (both increases and decreases), and pathophysiological signals such as cytokines. In response to the environmental stress, heat shock polypeptides use their ability to process other polypeptides to protect such polypeptides from any denaturation that may occur due to the presence of the stress. This mechanism also serves to protect cells which contain the protein.

Chaperonin polypeptides are a subgroup of heat shock polypeptides whose role in polypeptide folding is well known. There are two families of chaperonin polypeptide, the chaperonin 60 (approximately 60 kDa) and chaperonin 10 (approximately 10 kDa) families (Ranford, 2000). The best characterized chaperonins are those derived from *E. coli*, from which the characteristic structure of chaperonin 60 and chaperonin 10 has been established. The chaperonin complexes of most other organisms also substantially conform to this characteristic structure.

The characteristic structure of chaperonins is a complex formed from two heptamer rings (composed of seven chaperonin 60 monomers) which face one another and are capped by a heptamer ring composed of chaperonin 10 monomers.

Conventionally, chaperonins assist polypeptide folding when the target polypeptide enters the central core of the ringed heptamers, and on the subsequent release of energy from ATP the target polypeptide is released from the central core by a conformational change in the chaperonin structure (Ranson et al. (1998) *Review Article: Chaperones*. Biochem. J. (333): 233-242).

*Mycobacterium tuberculosis* (*M. tuberculosis*) produces Chaperonin 60.1 (cpn 60.1), a polypeptide that is named based on its amino acid sequence identity to other known chaperonins. Further *M. tuberculosis* chaperonin polypeptides are chaperonin 10 (cpn 10) and chaperonin 60.2 (cpn 60.2). Chaperonin 60.2 exhibits 59.6% amino acid sequence identity and 65.6% nucleic acid sequence identity to cpn 60.1.

Pain relief is usually achieved by oral or parenteral medication. Effective pain relief can be achieved in most cases with widely known pain relief drugs such as paracetamol, aspirin and other non-steroidal anti-inflammatory drugs (NSAIDS) such as ibuprofen, and cylooxygenase-2-selective inhibitors (CSIs). Narcotic analgesics act on specific receptors in the Central Nervous System (CNS). Codeine and dihydrocodeine are moderately potent narcotic analgesics and have a low potential for addiction. Other more potent narcotic analgesics, such as morphine and methadone can be used to control severe pain.

A variety of problems exist with presently known pain relief agents. The drugs are relatively short acting and analgesia lasts for only a few hours. Repeated doses of the drug are usually necessary to control the pain. Sub-optimal pain relief is another common problem, leading to the patient increasing the dose, or changing medication. In the case of NSAIDS, unpleasant gastrointestinal side-effects such as dyspepsia and ulcers are common, and about two-thirds of users change brands of NSAIDS at least once because of adverse effects and poor efficacy (Steinfeld S and Bjorke P A. Results from a patient survey to assess gastrointestinal burden of non-steroidal anti-inflammatory drug therapy contrasted with a review of data from EVA to determine satisfaction with rofecoxib. Rheumatology (Oxford) 2002, 41(S1), 23-27.). In addition, NSAIDs and CSIs can give rise to cardiovascular complications (Hillis W S, (2000) Areas of emerging interest in analgesia: cardiovascular complications. Am. J. Ther. 9 (3) 259-69). Aspirin can cause Reye Syndrome in a small proportion of children, and thus aspirin is not available for use in children. Paracetamol has to be used with caution since, an overdose, is hepatotoxic (Cranswick, N., Coghlan D. Paracetamol efficacy and safety in children: the first 40 years (2000) Am. J. Ther. 7(2) 135-41). Narcotic analgesics have a variety of side-effects including drowsiness, constipation, nausea, headache and vertigo. Repeated administration of potent narcotic analgesics such as morphine can cause addiction.

The present invention seeks to solve these problems in the following ways. An advantage of chaperonins as pain relief agents over current pain relief drugs is that they may have fewer adverse side-effects. It has been estimated that two billion people carry *M. tuberculosis* without developing Tuberculosis. Carriage of *M. tuberculosis* has not been associated with the side effects which are seen with commonly known pain-relief medication such as gastro-intestinal side-effects, cardiovascular complications, hepatotoxicity, Reye Syndrome or addiction.

A further advantage over previously known pain relief agents is that, the analgesic affect of chaperonins will last longer.

In a first aspect, the present invention provides the use of a heat shock polypeptide and/or its encoding nucleic acid sequence, in the manufacture of a medicament for use in the relief of pain.

Preferably the heat shock polypeptide is a chaperonin. More preferably the chaperonin is derived from a bacterium. Yet more preferably the chaperonin is derived from *Mycobacterium*. Most preferably the chaperonin is derived from *Mycobacterium tuberculosis*.

Preferably the nucleic acid comprises:

(i) the nucleotide sequence of FIG. 1 (SEQ ID NO:1) and/or FIG. 2 (SEQ ID NO:3) and/or FIG. 3 (SEQ ID NO:5), or (ii) a sequence which has more than 66% identity to sequence (i), or a sequence which hybridizes to sequence (i) under conditions of 2×SSC, 65° C. (wherein SCC=0.15M NaCl, 0.15M sodium citrate, pH 7.2) which encodes a functionally equivalent polypeptide to the sequence encoded by the nucleotide sequence of FIG. 1 (SEQ ID NO:1) and/or FIG. 2 (SEEQ ID NO:3) and/or FIG. 3 (SEQ ID NO:5), or (iii) a fragment of sequence (i) or (ii) encoding a functionally equivalent polypeptide fragment.

Preferably the heat shock polypeptide comprises:
(i) the amino acid sequence of FIG. 1 (SEQ ID NO:2) and/or FIG. 2 (SEQ ID NO:4) and/or FIG. 3 (SEQ ID No:6), or
(ii) a sequence which has more than 60% identity to sequence (i) which provides a functionally equivalent polypeptide, or
(iii) a functionally equivalent fragment of sequence (i) or (ii).

Preferably the functionally equivalent fragments are from 3 to 400 residues in length. Yet more preferably the functionally equivalent fragments are from 3 to 100 residues in length.

Preferably the nucleic acid molecule encodes a functionally equivalent fragment as defined above.

Preferably the medicament further comprises a pharmaceutically acceptable excipient, diluent or carrier.

More preferably the medicament is provided in combination with at least one additive for assisting or augmenting the action of the nucleic acid molecules or polypeptides.

Yet more preferably the additive is selected from at least one of paracetamol, aspirin and other non-steroidal anti-inflammatory drugs (NSAIDS) such as ibuprofen, and cylooxygenase-2-selective inhibitors (CSIs), opiates, such as morphine and heroin.

Preferably the medicament provides prolonged or sustained relief.

Preferably the daily dosage level of will be from 0.0001 to 100,000 mg, administered in single or divided doses. More preferably the daily dosage level is 0.0001 to 1000 mg.

In a preferred embodiment the time between dose administrations to the patient is between six and twelve hours.

Preferably the time between dose administrations to the patient is between nine and twelve hours after the previous dose.

In a further embodiment the time between dose administrations to the patient is between 12 days to 6 months. In a yet further preferred embodiment the time between dose administrations is between 12 hours to 12 days.

Preferably the compositions of the invention are formulated to permit administration by at least one selected from the intranasal, oral, parenteral, topical, ophthalmic, suppository, pessary or inhalation routes.

More preferably the compositions of the invention are formulated to permit administration by inhalation.

Preferably the medicament is used in pain relief of a human or animal patient. Most preferably the patient is a human.

In a second aspect, the present invention additionally provides a method comprising administering to a patient an amount of a medicament for the relief of pain, as described according to the first aspect of the invention.

DEFINITIONS

By "use in the relief of pain" we include any treatment which influences the pain felt by an individual, such influence including a delay in the onset, a reduction in the severity, a reduction of the duration, and/or the removal of the feeling of pain.

By "additive" we mean an ingredient that is provided in addition to the main medicament that is pharmacologically active either independently or in combination with the main medicament, whereby its presence in the medicament assists or augments the action of the main medicament.

By "hyperalgesia" we mean an earlier onset, an increase in the severity, an increase of the duration, and/or increased susceptibility to the feeling of pain.

By "functionally equivalent" we mean polypeptides and polypeptide fragments, which possess a pain relieving activity. This activity is preferably substantially the same or more preferably greater than the pain relieving activity of chaperonins derived from *Mycobacterium tuberculosis*.

Functional equivalence can be measured using the methods as described in the examples e.g. Paw latency on a heated plate.

By "polypeptide" we also include peptides, proteins and peptidomimetic compounds. The term "peptidomimetic" refers to a compound that mimics the conformation and desirable features of a particular peptide as a therapeutic agent, but that avoids the undesirable features.

By "identity" we mean the number or percentage (dependent on presentation of the results) of nucleic acid residues in a candidate sequence that are identical with the nucleic acid residues of the sequence of interest, after aligning the sequences and introducing gaps, if necessary to achieve maximum percent sequence identity, and not considering any conservative substitutions as part of the sequence identity. The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res.* 22, 4673-80). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

PREFERRED EMBODIMENTS

Examples embodying certain preferred aspects of the invention will now be described with reference to the following figures in which:—

PWL=Paw withdrawal latency

PWD=Paw withdrawal duration

VFF 4.31=Von Frey monofilament–4.31 calibre

VFF 5.07=Von Frey monofilament–5.07 calibre

FIG. 1—Amino acid (SEQ ID NO:2) and nucleic acid (SEQ ID NO:1) sequences of *Mycobacterium tuberculosis* Chaperonin 60.1.

FIG. 2—Amino acid (SEQ ID NO:4) and nucleic acid (SEQ ID NO:3) sequences of *Mycobacterium tuberculosis* Chaperonin 60.2.

FIG. 3—Amino acid (SEQ ID NO:6) and nucleic acid (SEQ ID NO:5) sequences of *Mycobacterium tuberculosis* Chaperonin 10.

FIG. 4—Vomes Fry testing of cpn 60.1. Shows the number of paw withdrawals per 10 trials with two different Von Frey monofilaments (4.31 and 5.07) in the presence and absence of Mt cpn 60.1.

Figure 5:
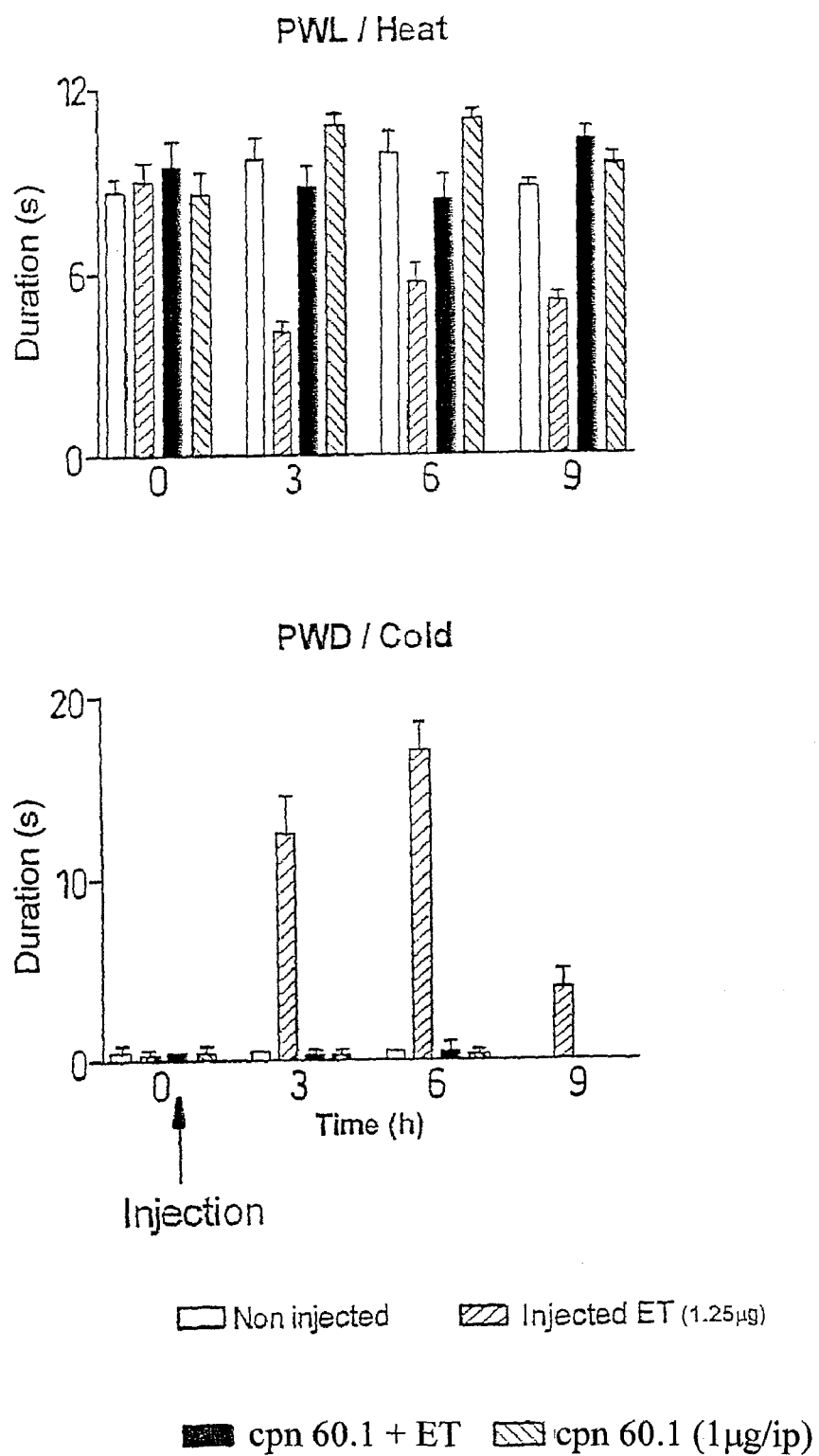

FIG. 5—PWL/PWD testing of cpn 60.1. Shows the duration of the responses of paw withdrawal in animals on the hot plate (upper panel) and on the cold plate (lower panel).

Figure 6:
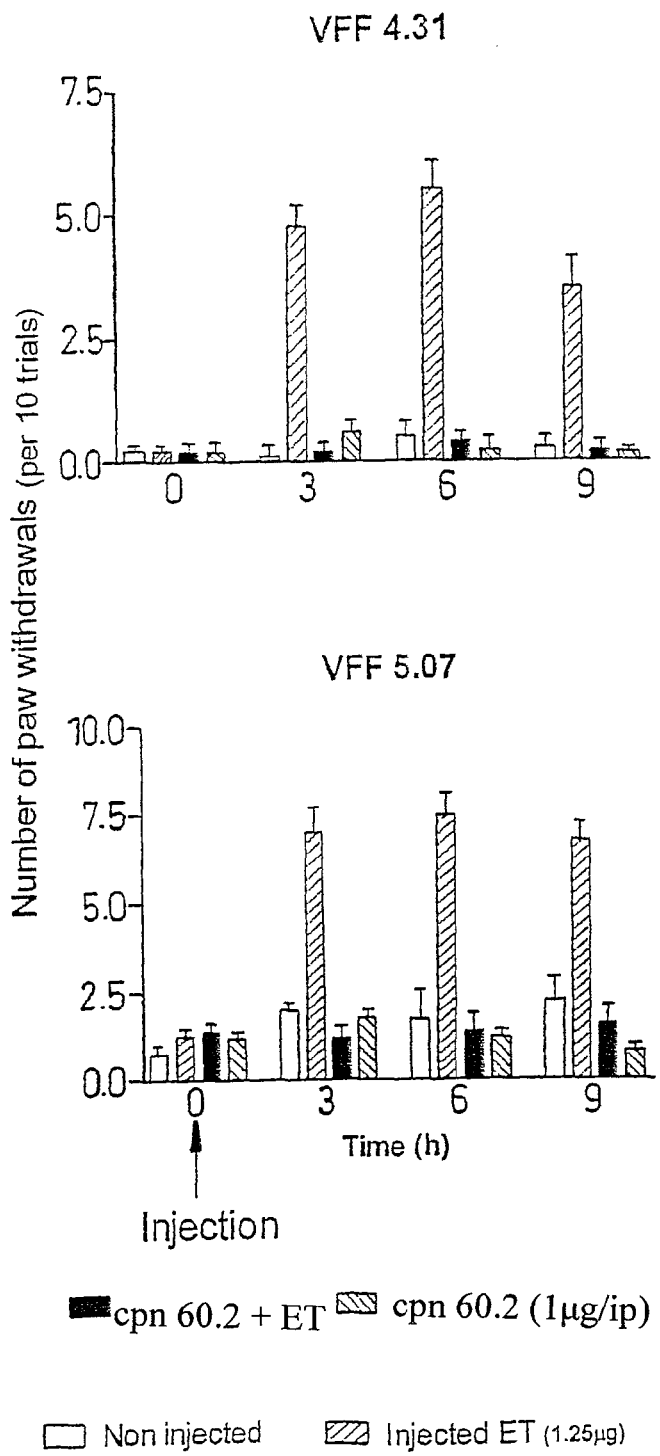

FIG. 6—Vomes Fry testing of Cpn 60.2. Shows the number of paw withdrawals per 10 trials with two different Von Frey microfilament calibers in the presence and absence of Mt cpn 60.1.

Figure 7:
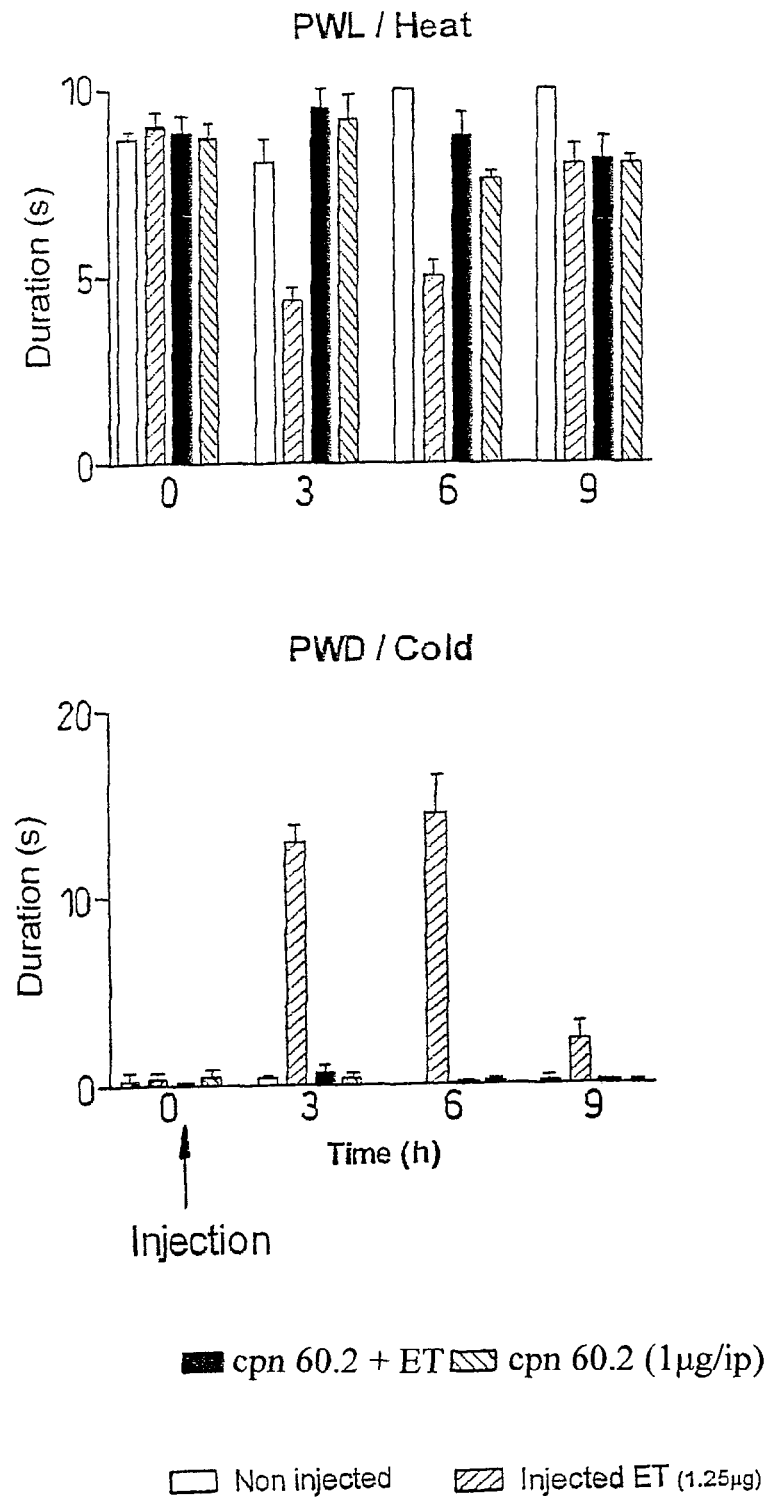

FIG. 7—PWL/PWD testing of Cpn 60.2. Shows the duration of the responses of paw withdrawal in animals on the hot plate (upper panel) and on the cold plate (lower panel).

Figure 8:
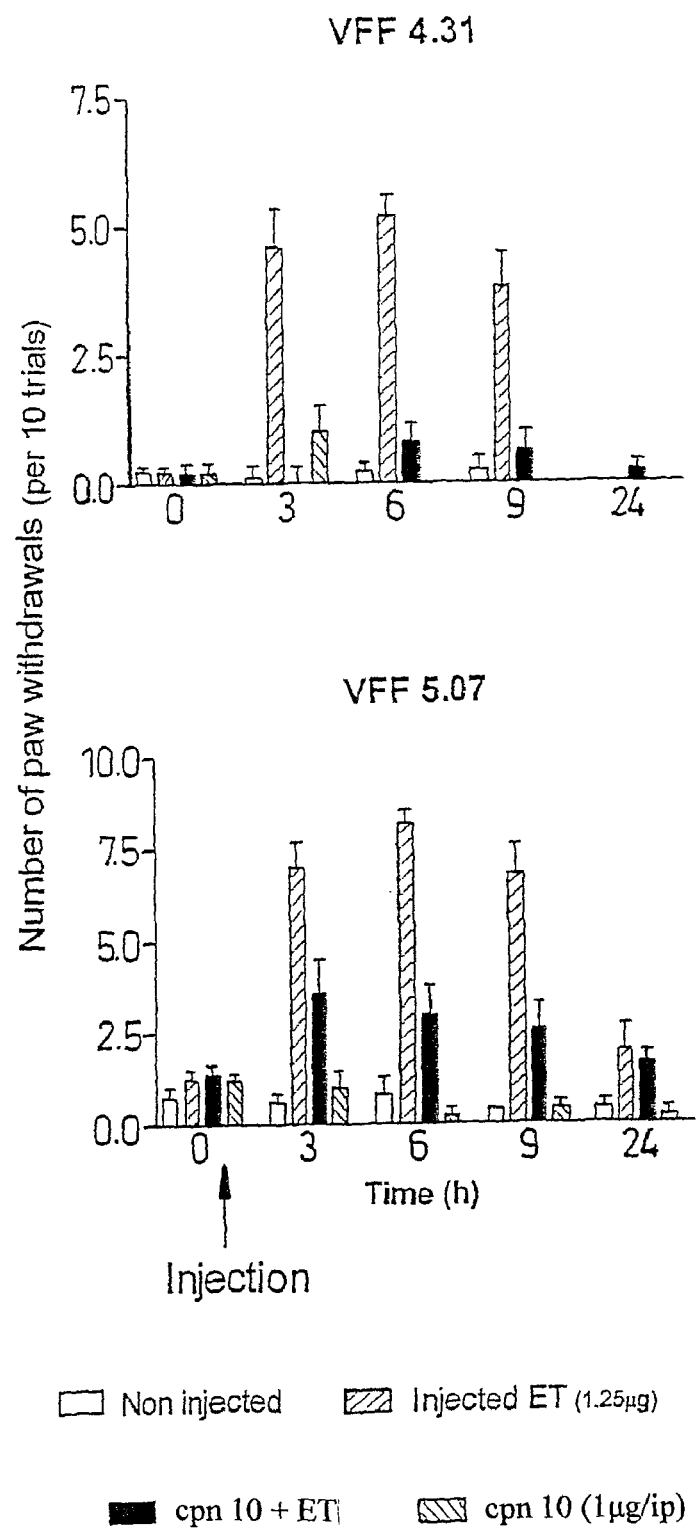

FIG. 8—Vomes Fry testing of cpn 10. Shows the number of paw withdrawals per 10 trials with two different Von Frey monofilaments in the presence and absence of Mtcpn10.

Figure 9:
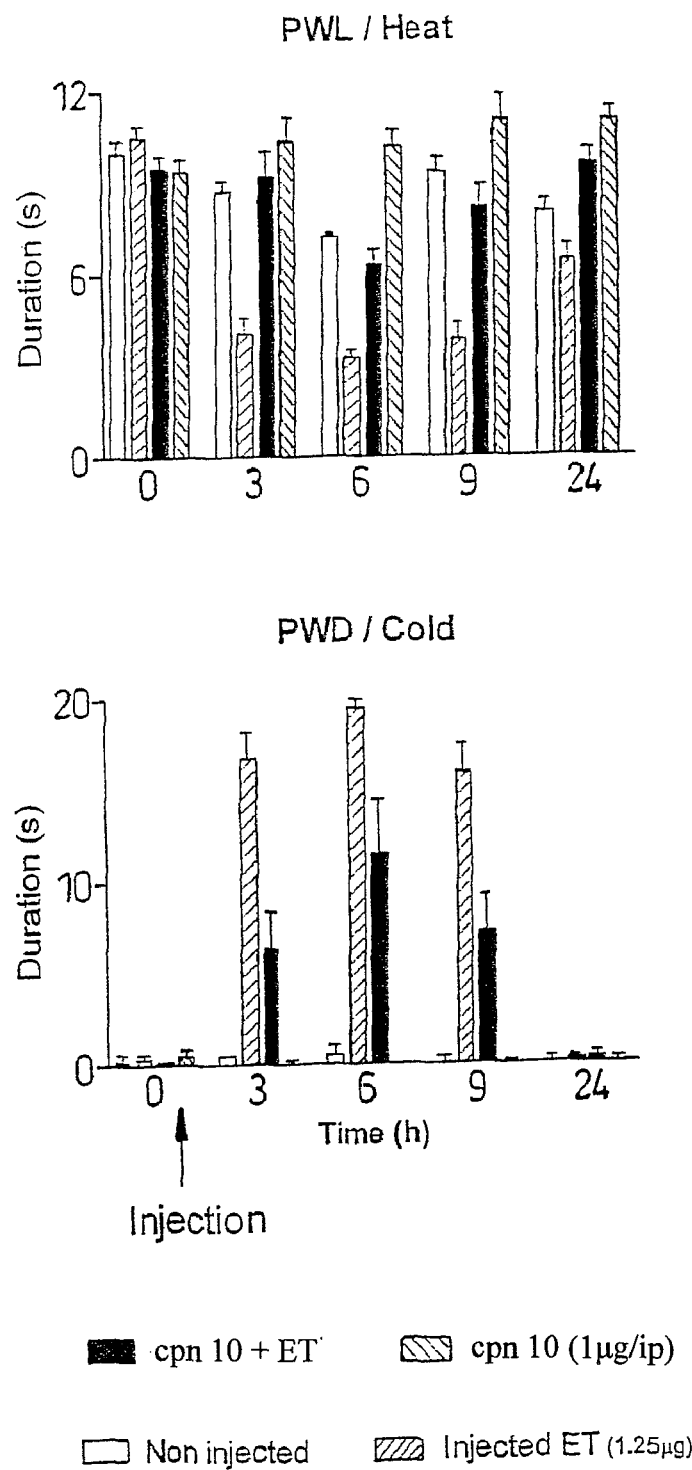

FIG. 9—PWL/PWD testing of cpn 10. Shows the duration of the responses of paw withdrawal in animals on the hot plate (upper panel) and on the cold plate (lower panel).

EXAMPLE 1

Experimental Testing of Heat Shock Polypeptides In Vivo

Experimental testing of heat shock polypeptides was investigated in test animals, separated into groups. Certain groups had induced hyperalgesia (i.e. an increased sensitivity to pain) and the effects of heat shock polypeptides on normal and hyperalgesic animals was observed and measured.

Methods and Materials

The analgesic effect of chaperonins can be measured using the model for inflammatory pain described in Kanaan et al. (1996) *Pain* 66, p3'73-3'79, the disclosure of which is incorporated herein by reference. This model is based on endotoxin (ET)-induced inflammatory hyperalgesia in rats and mice.

A brief description of the methods employed are presented below.

Adult (200-250 g) male Sprague-Dawley rats and adult (20-30 g) male Balb/c mice were used. The animals were separated into four groups:

Group 1—No injection.

Group 2—Endotoxin only.

Group 3—Endotoxin and Heat shock polypeptide.

Group 4—Heat shock polypeptide only.

Injection of Test Substrates

Groups 2 and 3 were injected subcutaneously into the left hind paw with 1.25 Tg ET prepared from *Salmonella typhosa*, 0901 (Difco, Detroit, Mich., USA). Groups 1 and 4 received no endotoxin but instead received sterile physiological saline injected in the same manner. Groups 3 and 4 additionally received 1 Tg/ip of heat shock polypeptide injected in the same manner but not same mixture.

Behavioral Observation

After injection, each animal was observed 48 hours.

Temperature Plate Test

The animals were individually placed on a hot surface plate in which the temperature was adjusted between 52.8 and 53.3° C., or a cold surface plate in which the temperature was adjusted between 4.8 and 5.3° C. The latency of the first sign of paw licking or jumping to avoid heating pain was taken as an index of the pain threshold.

Von Frey Monofilament Testing for Mechanical Allodynia

The method of Von Frey testing is disclosed in El-Khoury C et al. Neuroscience 2002, 112: 541-553 as incorporated herein.

Briefly, rats are placed in individual compartments of an elevated cage with a floor made of wire grid. The plantar surface of the hind paws is stimulated by Von Frey monofilaments (VFF) with increasing force. Two different monofilaments are used of different calibers (VFF 4.31 (lowest) and VFF 5.07 (highest)) in the range of 15-18.5 mN and 100-110 mN respectively. Paw withdrawals per 10 trials are recorded.

Experimental Protocols and Data Analysis

To determine the effects of an ET and/or heat shock polypeptide, a set (n=5) of animals with representatives of each group (1 to 4) were subjected to the pain test for 3 consecutive days. Each animal was subjected to pain tests at the time intervals of 3, 6, 9 and 24 hours after the ET injection.

The degree of significance of variations between control and experimental values for each pain test was assessed by ANOVA test.

Heat Shock Polypeptides Tested

The preferred methods were tested with the *Mycobacterium tuberculosis* chaperonin polypeptides, cpn 60.1, cpn 60.2 and cpn 10. Synthesis of these proteins can be achieved by using the sequences encoding the polypeptide constituting the compound of the invention as disclosed herein in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810,648 issued 7 Mar. 1989 to Stalker, all of which are incorporated herein by reference.

Results

The results are shown in FIGS. 4 to 9 and it is clear that all three of the chaperonins tested exhibit a strong analgesic effect.

EXAMPLE 2

Analgesic Effect of cpn 60.1

FIG. 4 shows the number of paw withdrawals per 10 trials with two different Von Frey monofilaments (4.31 and 5.07) in the presence and absence of *M. tuberculosis* cpn 60.1. Both tests gave the same broad pattern of results.

In track one of each time point, the negative control had a background of approximately one PWD. In track two, the positive control (injected ET or lipopolysacccharide) increased to a maximum of about 6 (VFF 4.31) and 9.5 (VFF 5.07) PWD. Track three, demonstrates the effect of cpn 60.1 treatment of ET induced hyperalgesia, and shows a general reduction to background levels in PWD at time points 3-9 hours. Track 4 shows the effect of cpn60.1 injected on its own, i.e. that there is no difference over that seen in the non-injected control group.

These results demonstrate that cpn60.1 reduces the hyperalgesia which is induced by endotoxin.

FIG. 5 shows the duration of the responses of paw withdrawal in animals on the hot plate (PWL/Heat) and on the cold plate (PWD/Cold). The hot plate results show that there is no difference between the different time points and treatments, except for ET treated animals at time points 3-9 hours when the duration of latency is reduced to 4-5 seconds. The cold plate results show that none of the PWD are above the background with the exception of endotoxin injection, which shows a raised PWD at time points 3-9 hours. These results indicate that cpn 60.1 reduces hyperalgesia which is induced by endotoxin.

EXAMPLE 3

Analgesic Effect of cpn 60.2

FIG. 6 shows the number of paw withdrawals per 10 trials with two different Von Frey microfilament calibers (VFF 4.31 and VFF 5.07) in the presence and absence of *M. tuberculosis* cpn 60.2. Both tests broadly give the same pattern of results.

In track one of each time point, the negative control had a background of approximately less than one PWD in VFF4.31 and less than 2.5 PWD in VFF 5.07. In track two, the positive control (injected ET or lipopolysacccharide) increased to a maximum of about 6 (VFF4.31) and 7.5 (VFF5.07) PWD. In track three, the effect of cpn 60.2 treatment on ET induced hyperalgesia is shown, this demonstrates a reduction to background levels (control levels) in PWD at time points 3-9 hours. Track 4 shows the effect of cpn 60.2 injected on its own such that there is no effect over that seen in the non-injected control group. These results demonstrate that cpn 60.2 reduces the hyperalgesia which is induced by endotoxin.

FIG. 7 shows the duration of the responses of paw withdrawal in animals on the hot plate (PWL/Heat) and on the cold plate (PWD/Cold). The hot plate results show that there is no difference between the different time points and treatments, except for ET treated animals at time points 3 and 6 hours when the duration of latency is reduced to 4-5 seconds. The cold plate results show that none of the PWD are above the background with the exception of ET which is considerably raised at time points 3-9 hours. These results indicate that this cpn 60.2 reduces hyperalgesia which is induced by endotoxin.

EXAMPLE 4

Analgesic Effect of cpn 10

FIG. 8 shows the number of paw withdrawals per 10 trials with two different Von Frey monofilaments (VFF 4.31 and VFF 5.07) in the presence and absence of *M. tuberculosis* cpn 10. Both tests broadly give the same pattern of results.

In track one of each time point, the negative control had a background of approximately less than one PWD. In track two, the positive control (injected ET or lipopolysacccharide) increased to a maximum of about 6 (VFF 4.31) and 8 (VFF 5.07) PWD. In track three, the effect of cpn 10 treatment of ET induced hyperalgesia on PWD is shown, for VFF 4.31 there is a reduction to background levels in PWD at time point 3 hours and just above background at time points 6 and 9 hours. For VFF 5.07 cpn 10 shows a smaller reduction, to 3.5 at 3 hours, to 3 at 6 hours, to 2.5 at 9 hours and no reduction at 24 hours. Track 4 shows the effects of cpn 10 injected on its own which demonstrates no effect over that seen in the non-injected group, except for VFF 4.31 where cpn 10 induced approximately one PWD at the 3 hour time point. These results demonstrate that cpn 10 reduces the hyperalgesia which is induced by ET.

FIG. 9 shows the duration of the responses of paw withdrawal in animals on the hot plate (PWL/Heat) and on the cold plate (PWD/Cold). The heat plat test shows that there is no marked difference between the different time points and treatments, except for ET treated animals at time points 3-9 hours when the duration is reduced to 4-5 seconds. The cold plate test shows that none of the PWD are above the background with the exception of ET and ET in combination with cpn 10 which is considerably raised at time points 3-9 hours. At these time points cpn 10 still reduced the duration by about 50%.

Hence, cpn 10 is effective at reducing endotoxin induced hyperalgesia.

EXAMPLE 5

Pharmaceutical Compositions

A further aspect of the invention provides a pharmaceutical formulation comprising a heat shock polypeptide (the medicament) in admixture with a pharmaceutically or veterinarily acceptable adjuvant, diluent or carrier that is selected with regard to the intended route of administration and standard pharmaceutical practice. The carrier(s) must be "acceptable" in the sense of being compatible with the compound of the invention and not deleterious to the recipients thereof. Typically, the carriers will be water or saline which will be sterile and pyrogen free.

The formulations may conveniently be presented in unit dosage form containing a daily dose or unit or an appropriate fraction thereof, of the medicament and may be prepared by any of the methods well known in the art of pharmacy. Such methods include the step of bringing into association the medicament with the carrier which constitutes one or more accessory ingredients. In general the formulations are prepared by uniformly and intimately bringing into association the medicament with liquid carriers or finely divided solid carriers or both, and then, if necessary, shaping the product.

The compounds of the invention can be administered orally or by any parenteral route, in the form of a pharmaceutical formulation comprising the medicament, optionally in the form of a non-toxic organic, or inorganic, acid, or base, addition salt, in a pharmaceutically acceptable dosage form.

Depending upon the disorder and patient to be treated, as well as the route of administration, the compositions may be administered at varying doses.

The compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatine and acacia. Additionally, lubricating agents such as magnesium stearate, stearic acid, glyceryl behenate and talc may be included.

Solid compositions of a similar type may also be employed as fillers in gelatine capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 0.0001 to 100,000 mg per adult, administered in single or divided doses.

Thus, for example, the tablets or capsules of the compound of the invention may contain from 0.0001 mg to 100,000 mg of active compound for administration singly or two or more at a time, as appropriate. It is envisaged that a 500 mg tablet or capsule would be appropriate for single, repeat doses of one or more tablets or capsules. The physician in any event will determine the actual dosage, which will be most suitable for each individual patient, and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatine) for use in an inhaler or insufflator may be formulated to contain a powder mix of a compound of the invention and a suitable powder base such as lactose or starch.

Aerosol or dry powder formulations are preferably arranged so that each metered dose or "puff" contains between 0.001 mg and 2 g of a compound of the invention for delivery to the patient. It will be appreciated that he overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the medicament in a flavoured basis, usually sucrose and acacia or tragacanth; pastilles comprising the medicament in an inert basis such as gelatine and glycerin, or sucrose and acacia; and mouthwashes comprising the medicament in a suitable liquid carrier.

Generally, in humans, oral, topical or inhalation administration of the compounds of the invention is preferred, being the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration that will be most appropriate for a particular animal.

EXAMPLE 6

Methods of Pain Relief

The compounds of the invention will provide effective pain relief in the following incidences of pain: backache, headache, toothache, earache, Arthritis, Gout, soft tissue trauma, ligament/tendon traumatic damage, broken bones, cancer, post operative pain, menstrual pain, obstetric pain, renal tract pain, visceral pain, burns, abscesses and other infections.

The suggested treatment route and regimen for the treatment of any of these conditions is the administration of 0.1 mg to 1 gram once every 12 hours by inhalation delivered via an inhaler. However the skilled person would know that the most appropriate treatment regime would be dependent on the individual and the severity of the pain being felt.

The invention claimed is:

1. A method of relieving pain comprising administering, to a subject in need thereof, a heat shock polypeptide or a nucleotide molecule encoding a heat shock polypeptide,
   wherein the heat shock polypeptide is a chaperonin,
   wherein the nucleotide molecule comprises
   at least one nucleotide sequence comprising one or more of the nucleotide sequence of SEQ ID NOs: 1, 3, and 5.

2. A method of relieving pain comprising administering, to a subject in need thereof, a heat shock polypeptide or a nucleotide molecule encoding a heat shock polypeptide,
   wherein the heat shock polypeptide is a chaperonin,
   wherein the polypeptide comprises
   at least one amino acid sequence comprising one or more of the amino acid sequence of SEQ ID NOs: 2, 4, and 6.

3. The method of claim 1 or 2, wherein the heat shock polypeptide is isolated or cloned from a bacterium.

4. The method of claim 3, wherein the bacterium is a *Mycobacterium*.

5. The method of claim 4, wherein the *Mycobacterium* is *Mycobacterium tuberculosis*.

6. The method of claim 1 or 2, wherein said heat shock polypeptide or said nucleotide molecule is administered in a composition comprising a pharmaceutically acceptable excipient, diluent or carrier.

7. The method of claim 1 or 2, wherein said heat shock polypeptide or said nucleotide molecule is administered in a composition comprising at least one additive for assisting or augmenting the pain relief action by the nucleotide molecule or polypeptide.

8. The method of claim 7, wherein the additive is selected from at least one member of the group consisting of paracetamol, aspirin, ibuprofen, another non-steroidal anti-inflammatory drug (NSAID), a cylooxygenase-2-selective inhibitor (CSI), and an opiate.

9. The method of claim 7, wherein the composition provides prolonged or sustained pain relief.

10. The method of claim 1 or 2, wherein said heat shock polypeptide or nucleotide molecule encoding a heat shock polypeptide are administered in single or divided doses at a daily dosage level of from 0.0001 to 100,000 mg.

11. The method of claim 10, wherein said daily dosage level is from 0.0001 to 1000 mg.

12. The method of claim 10, wherein the divided doses are administered between six and twelve hours apart.

13. The method of claim 12, wherein the divided doses are administered between nine and twelve hours apart.

14. The method of claim 10, wherein the divided doses are administered between twelve hours and twelve days apart.

15. The method of claim 10, wherein the divided doses are administered between twelve days and six months apart.

16. The method of claim 6, wherein the composition is formulated to permit administration by at least one route selected from the group consisting of intranasal, oral, parenteral, topical, ophthalmic, suppository, pessary and inhalation.

17. The method of claim 16, wherein the composition is formulated to permit administration by inhalation.

18. The method of claim 1 or 2, wherein the subject is a human or animal.

19. The method of claim 18, wherein the subject is a human.

20. The method of claim 1 or 2, wherein the pain is due to at least one member selected from the group consisting of backache, headache, toothache, earache, arthritis, gout, soft tissue trauma, ligament/tendon traumatic damage, a broken bone, cancer, post operative pain, menstrual pain, obstetric pain, renal tract pain, visceral pain, a burn, an abscess and an infection.

* * * * *